(12) United States Patent
Umemoto et al.

(10) Patent No.: US 9,630,919 B2
(45) Date of Patent: *Apr. 25, 2017

(54) INDUSTRIAL METHODS FOR PRODUCING ARYLSULFUR PENTAFLUORIDES

(71) Applicant: UBE Industries, Ltd., Yamaguchi (JP)

(72) Inventors: Teruo Umemoto, Westminster, CO (US); Norimichi Saito, Superior, CO (US)

(73) Assignee: UBE INDUSTRIES, LTD. (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/246,197

(22) Filed: Aug. 24, 2016

(65) Prior Publication Data

US 2016/0362365 A1 Dec. 15, 2016

Related U.S. Application Data

(62) Division of application No. 14/799,337, filed on Jul. 14, 2015, now Pat. No. 9,447,034, which is a division of application No. 13/985,553, filed as application No. PCT/JP2012/053905 on Feb. 14, 2012, now Pat. No. 9,108,910.

(60) Provisional application No. 61/442,927, filed on Feb. 15, 2011.

(51) Int. Cl.
*C07C 303/04* (2006.01)
*C07C 381/00* (2006.01)
*C07C 321/28* (2006.01)

(52) U.S. Cl.
CPC .......... *C07C 381/00* (2013.01); *C07C 321/28* (2013.01)

(58) Field of Classification Search
USPC ........................................ 562/821, 824, 826
See application file for complete search history.

(56) References Cited

U.S. PATENT DOCUMENTS

| | | | |
|---|---|---|---|
| 8,653,302 B2 * | 2/2014 | Umemoto | ............. C07C 381/00 562/821 |
| 9,108,910 B2 | 8/2015 | Umemoto et al. | |
| 2004/0249209 A1 | 12/2004 | Bailey et al. | |
| 2015/0315139 A1 | 11/2015 | Umemoto et al. | |

FOREIGN PATENT DOCUMENTS

| | | |
|---|---|---|
| WO | 2008/118787 A1 | 10/2008 |
| WO | 2010/014665 A1 | 2/2010 |
| WO | 2012/111839 | 8/2012 |

OTHER PUBLICATIONS

International Search Report for PCT/JP2012/053905, mailed Jul. 16, 2012.
Written Opinion of the ISA for PCT/JP2012/053905, mailed Jul. 16, 2012.
International Preliminary Report on Patentability for PCT/JP2012/053905, mailed Aug. 21, 2013.

* cited by examiner

*Primary Examiner* — Pancham Bakshi
(74) *Attorney, Agent, or Firm* — Swanson & Bratschun, L.L.C.

(57) ABSTRACT

Industrial methods for producing arylsulfur pentafluorides are disclosed. Methods include reacting arylsulfur halotetrafluoride with hydrogen fluoride in the absence or presence of one or more additives selected from a group of fluoride salts, non-fluoride salts, and unsaturated organic compounds to form arylsulfur pentafluorides.

3 Claims, No Drawings

INDUSTRIAL METHODS FOR PRODUCING ARYLSULFUR PENTAFLUORIDES

RELATED APPLICATIONS

This application is a divisional of U.S. application Ser. No. 14/799,337 filed Jul. 14, 2015, entitled "Industrial Methods for Producing Arylsulfur Pentafluorides", which is a divisional of U.S. application Ser. No. 13/985,553, filed Aug. 14, 2013, entitled "Industrial Methods for Producing Arylsulfur Pentafluorides", which is a 35 U.S.C. §371 national phase application of PCT/JP2012/053905 (WO 2012/111839), filed on Feb. 14, 2012, entitled "Industrial Methods for Producing Arylsulfur Pentafluorides", which application claims the benefit of U.S. Provisional Application Ser. No. 61/442,927, filed Feb. 15, 2011, each of which are incorporated herein by reference in their entirety. Any disclaimer that may have occurred during the prosecution of the above-referenced applications is hereby expressly rescinded, and reconsideration of all relevant art is respectfully requested.

TECHNICAL FIELD

The invention relates to industrial methods useful in the production of arylsulfur pentafluorides.

BACKGROUND ART

Arylsulfur pentafluoride compounds are used to introduce one or more sulfur pentafluoride groups into various commercial organic molecules. In particular, arylsulfur pentafluorides are useful (as product or intermediate) in the development of liquid crystals (Eur. J. Org. Chem. 2005, pp. 3095-3100) and as bioactive chemicals such as fungicides, herbicides, insecticides, paraciticides, anti-cancer drugs, enzyme inhibitors, antimalarial agent, and other like materials [see, for example, J. Pestic. Sci., Vol. 32, pp. 255-259 (2007); Chimia Vol. 58, pp. 138-142 (2004); Chem Bio Chem 2009, 10, pp. 79-83; Tetrahedron Lett. Vol. 51 (2010), pp. 5137-5140; J. Med. Chem. 2011, Vol. 54, pp. 3935-3949; J. Med. Chem. 2011, Vol. 54, pp. 5540-5561; WO 99/47139; WO 2003/093228; WO 2006/108700 A1; US 2005/0197370; U.S. Pat. No. 7,381,841 B2; US 2008/176665; U.S. Pat. No. 7,446,225 B2; WO 2010/138588 A2; WO 2011/44184].

Arylsulfur pentafluorides have been synthesized using one of the following synthetic methods: (1) fluorination of diaryl disulfies or arylsulfur trifluoride with $AgF_2$ [see J. Am. Chem. Soc., Vol. 82 (1962), pp. 3064-3072, and J. Fluorine Chem. Vol. 112 (2001), pp. 287-295]; (2) fluorination of bis(nitrophenyl) disulfides, nitrobenzenethiols, or nitrophenylsulfur trifluorides with molecular fluorine ($F_2$) [see Tetrahedron, Vol. 56 (2000), pp. 3399-3408; Eur. J. Org. Chem., Vol. 2005, pp. 3095-3100; and U.S. Pat. No. 5,741,935]; (3) fluorination of diaryl disulfides or arenethiols with $F_2$, $CF_3OF$, or $CF_2(OF)_2$ in the presence or absence of a fluoride source (see US Patent Publication No. 2004/0249209 A1); (4) fluorination of diaryl disulfides with $XeF_2$ [see J. Fluorine Chem., Vol. 101 (2000), pp. 279-283]; (5) reaction of 1,4-bis(acetoxy)-2-cyclohexene with $SF_5Br$ followed by dehydrobromination or hydrolysis and then aromatization reactions [see J. Fluorine Chem., Vol. 125 (2004), pp. 549-552]; (6) reaction of 4,5-dichloro-1-cyclohexene with $SF_5Cl$ followed by dehydrochlorination [see Organic Letters, Vol. 6 (2004), pp. 2417-2419 and PCT WO 2004/011422 A1]; and (7) reaction of $SF_5Cl$ with acetylene, followed by bromination, dehydrobromination, and reduction with zinc, giving pentafluorosulfanylacetylene, which was then reacted with butadiene, followed by an aromatization reaction at very high temperature [see J. Org. Chem., Vol. 29 (1964), pp. 3567-3570].

Each of the above synthetic methods has one or more drawbacks making it either impractical (time and/or yield), overly expensive, and/or overly dangerous to practice. For example, synthetic methods (1) and (4) provide low yields and require expensive reaction agents, e.g., $AgF_2$ and $XeF_2$. Methods (2) and (3) require the use of $F_2$, $CF_3OF$, or $CF_2(OF)_2$, each of which is a toxic, explosive, and/or corrosive gas, and products produced using these methods are at a relatively low yield. Note that handling of these gasses is expensive from the standpoint of production, storage and use. In addition, synthetic methods that require the use of $F_2$, $CF_3OF$, and/or $CF_2(OF)_2$ are limited to the production of deactivated arylsulfur pentafluorides, such as nitrophenylsulfur pentafluorides, due to their extreme reactivity, which leads to side-reactions such as fluorination of the aromatic rings when not deactivated. Methods (5) and (6) also require expensive reactants, e.g., $SF_5Cl$ or $SF_5Br$, and have narrow application because the starting cyclohexene derivatives have limited availability. Finally, method (7) requires an expensive reactant, $SF_5Cl$, and this method includes numerous steps to reach the arylsulfur pentafluorides (timely and low yield).

As discussed above, conventional synthetic methodologies for the production of arylsulfur pentafluorides have proven difficult and are a concern within the art.

Recently, useful methods have been developed for solving the problems discussed above (see WO 2008/118787 A1; WO2010/014665 A1; US 2010/0130790 A1; US 2011/0004022 A1; U.S. Pat. Nos. 7,592,491 B2; 7,820,864 B2; 7,851,646 B2). One of the key steps described in each of these methods is the reaction of an arylsulfur halotetrafluoride with a fluoride source such as various fluorides compounds including elements found in groups 1, 2, 13-17 and transition elements of the Periodical Table. In particular, hydrogen fluoride is a useful fluoride source for the industrial process because of its availability and low cost, and in addition, its liquid nature having a boiling point 19° C. The liquid nature of hydrogen fluoride is suitable for large scale industrial processes because of its transportability, fluidity, and recyclability compared to solids, such as the fluorides of transition elements. However, methods using hydrogen fluoride still have several drawbacks, including: (1) as hydrogen fluoride is severely toxic, the amount of hydrogen fluoride used for a reaction must be minimized for safety and for the sake of the environment; (2) there is evolution of a large amount of a gaseous, toxic, corrosive hydrogen halide such as HCl (bp of HCl, −85° C.) from the reaction of an arylsulfur halotetrafluoride and hydrogen fluoride; (3) in some cases, a low yield or less purity of the product is obtained, because byproducts such as chlorinated arylsulfur pentafluorides are formed by side-reactions. These drawbacks cause significant cost problems in the industrial production of arylsulfur pentafluorides.

The present invention is directed toward finding more suitable methods to produce arylsulfur pentafluorides in an industrial scale and overcoming one or more of the problems discussed above.

SUMMARY OF INVENTION

Embodiments of the present invention provide a method suitable for the industrial production of arylsulfur pentafluoride, as represented by formula (I):

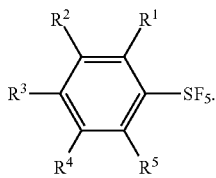

(I)

arylsulfur halotetrafluoride having a formula (II), shown below, is reacted with anhydrous hydrogen fluoride (HF) to form arylsulfur pentafluoride (formula I): a molar ratio of the arylsulfur halotetrafluoride to the anhydrous hydrogen fluoride (the arylsulfur halotetrafluoride/the anhydrous hydrogen fluoride) is in the range of about 1/10 to about 1/150.

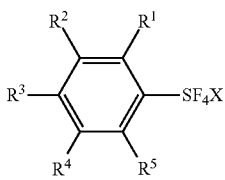

(II)

Embodiments of the present invention also provide methods for producing arylsulfur pentafluoride (formula I), in which arylsulfur halotetrafluoride is reacted with hydrogen fluoride in the presence of an additive to form arylsulfur pentafluoride. The additive is selected from a group consisting of fluoride salts having a formula, $M^+F^-(HF)_n$, non-fluoride salts having a formula, $M^+Y^-$, and organic compounds having one or more unsaturated bonds (in a molecule).

These and various other features as well as advantages which characterize embodiments of the invention will be apparent from a reading of the following detailed description and a review of the appended claims.

DESCRIPTION OF EMBODIMENTS

Embodiments of the present invention provide industrially useful methods for producing arylsulfur pentafluorides, as represented by formula (I). Prepared arylsulfur pentafluorides can be used, for among other things, to introduce one or more sulfur pentafluoride ($SF_5$) groups into various target organic compounds. As noted in the Background of the present disclosure, these target organic molecules, after introduction of the one or more sulfur pentafluoride groups, are useful as medicines, agrochemicals or liquid crystals. The methods of the invention provide an industrial, cost-effective method for producing arylsulfur pentafluorides of high purity and in high yield. The target organic compounds for purposes of the present disclosure typically include at least one target substitution site for modification by an $SF_5$.

Embodiments of the invention include a method which comprises reacting an arylsulfur halotetrafluoride, represented by formula (II), with hydrogen fluoride to form the arylsulfur pentafluoride having a formula (I), in which a molar ratio of an arylsulfur halotetrafluoride/hydrogen fluoride is in the range of about 1/10 to about 1/150, preferably about 1/15 to about 1/100, and furthermore, about 1/15 to about 1/50 (see for example Scheme 1, Process I).

Scheme 1: Process I

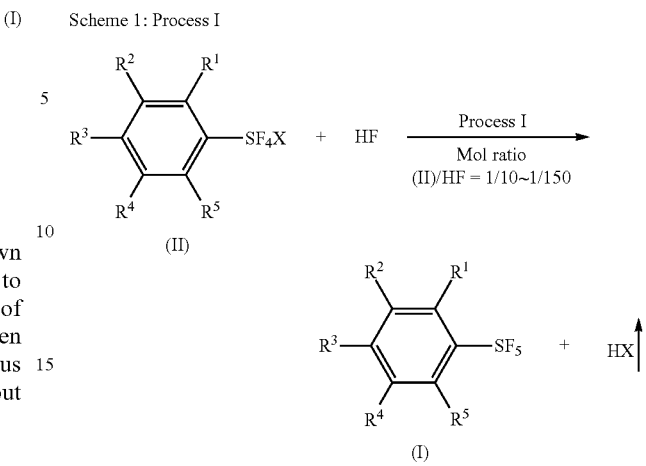

With regard to the compounds of formulas (I) and (II): substituents $R^1$, $R^2$, $R^3$, $R^4$, and $R^5$ each is independently a hydrogen atom; a halogen atom that is a fluorine atom, a chlorine atom, a bromine atom, or an iodine atom; a substituted or unsubstituted alkyl group having from 1 to 18 carbon atoms, preferably from 1 to 10 carbon atoms; a substituted or unsubstituted aryl group having from 6 to 30 carbon atoms, preferably from 6 to 15 carbon atoms; a nitro group; a cyano group; a substituted or unsubstituted alkanesulfonyl group having from 1 to 18 carbon atoms, preferably from 1 to 10 carbon atoms; a substituted or unsubstituted arenesulfonyl group having from 6 to 30 carbon atoms, preferably from 6 to 15 carbon atoms; a substituted or unsubstituted alkoxy group having from 1 to 18 carbon atoms, preferably from 1 to 10 carbon atoms; a substituted or unsubstituted aryloxy group having from 6 to 30 carbon atoms, preferably from 6 to 15 carbon atoms; a substituted or unsubstituted acyloxy group having from 1 to 18 carbon atom, preferably from 1 to 10 carbon atoms; a substituted or unsubstituted alkanesulfonyloxy group having from 1 to 18 carbon atom, preferably from 1 to 10 carbon atoms; a substituted or unsubstituted arenesulfonyloxy group having from 6 to 30 carbon atoms, preferably from 6 to 15 carbon atoms; a substituted or unsubstituted alkoxycarbonyl group having 2 to 18 carbon atoms, preferably from 2 to 10 carbon atoms; a substituted or unsubstituted aryloxycarbonyl group having 7 to 30 carbon atoms, preferably from 7 to 15 carbons; a substituted carbamoyl group having 2 to 18 carbon atoms, preferably from 2 to 10 carbon atoms; a substituted amino group having 1 to 18 carbon atoms, preferably from 1 to 10 carbon atoms; or a $SF_5$ group.

With regard to X, in a formula (II), X is a chlorine atom, a bromine atom, or an iodine atom.

The term "alkyl" as used herein is linear, branched, or cyclic alkyl. The alkyl part of alkanesulfonyl, alkoxy, alkanesulfonyloxy, or alkoxycarbonyl group as used herein is also linear, branched, or cyclic alkyl part.

The term "substituted alkyl" as used herein means an alkyl moiety having one or more substituents such as a halogen atom, a substituted or unsubstituted aryl group, and any other group with or without a heteroatom(s) such as an oxygen atom(s), a nitrogen atom(s), and/or a sulfur atom(s), which does not limit reactions of this invention.

The term "substituted aryl" as used herein means an aryl moiety having one or more substituents such as a halogen atom, a substituted or unsubstituted alkyl group, and any other group with or without a heteroatom(s) such as an oxygen atom(s), a nitrogen atom(s), and/or a sulfur atom(s), which does not limit reactions of this invention.

The term "substituted alkanesulfonyl" as used herein means an alkanesulfonyl moiety having one or more substituents such as a halogen atom, a substituted or unsubstituted aryl group, and any other group with or without a heteroatom(s) such as an oxygen atom(s), a nitrogen atom(s), and/or a sulfur atom(s), which does not limit reactions of this invention.

The term "substituted arenesulfonyl" as used herein means an arenesulfonyl moiety having one or more substituents such as a halogen atom, a substituted or unsubstituted alkyl group, and any other group with or without a heteroatom(s) such as an oxygen atom(s), a nitrogen atom(s), and/or a sulfur atom(s), which does not limit reactions of this invention.

The term "substituted alkoxy" as used herein means an alkoxy moiety having one or more substituents such as a halogen atom, a substituted or unsubstituted aryl group, and any other group with or without a heteroatom(s) such as an oxygen atom(s), a nitrogen atom(s), and/or a sulfur atom(s), which does not limit reactions of this invention.

The term "substituted aryloxy" as used herein means an aryloxy moiety having one or more substituents such as a halogen atom, a substituted or unsubstituted alkyl group, and any other group with or without a heteroatom(s) such as an oxygen atom(s), a nitrogen atom(s), and/or a sulfur atom(s), which does not limit reactions of this invention.

The term "substituted acyloxy" as used herein means an acyloxy moiety having one or more substituents such as a halogen atom, a substituted or unsubstituted alkyl group, a substituted or unsubstituted aryl group, and any other group with or without a heteroatom(s) such as an oxygen atom(s), a nitrogen atom(s), and/or a sulfur atom(s), which does not limit reactions of this invention.

The term "substituted alkanesulfonyloxy" as used herein means an alkanesulfonyloxy moiety having one or more substituents such as a halogen atom, a substituted or unsubstituted aryl group, and any other group with or without a heteroatom(s) such as an oxygen atom(s), a nitrogen atom(s), and/or a sulfur atom(s), which does not limit reactions of this invention.

The term "substituted arenesulfonyloxy" as used herein means an arenesulfonyloxy moiety having one or more substituents such as a halogen atom, a substituted or unsubstituted alkyl group, and any other group with or without a heteroatom(s) such as an oxygen atom(s), a nitrogen atom(s), and/or a sulfur atom(s), which does not limit reactions of this invention.

The term "substituted alkoxycarbonyl" as used herein means an alkoxycarbonyl moiety having one or more substituents such as a halogen atom, a substituted or unsubstituted aryl group, and any other group with or without a heteroatom(s) such as an oxygen atom(s), a nitrogen atom(s), and/or a sulfur atom(s), which does not limit reactions of this invention.

The term "substituted aryloxycarbonyl" as used herein means an aryloxycarbonyl moiety having one or more substituents such as a halogen atom, a substituted or unsubstituted alkyl group, and any other group with or without a heteroatom(s) such as an oxygen atom(s), a nitrogen atom(s), and/or a sulfur atom(s), which does not limit reactions of this invention.

The term "substituted carbamoyl" as used herein means a carbamoyl moiety having one or more substituents such as a substituted or unsubstituted alkyl group, a substituted or unsubstituted aryl group, and any other group with or without a heteroatom(s) such as an oxygen atom(s), a nitrogen atom(s), and/or a sulfur atom(s), which does not limit reactions of this invention.

The term "substituted amino" as used herein means an amino moiety having one or more substituents such as a substituted or unsubstituted acyl group, a substituted or unsubstituted alkanesulfonyl group, a substituted or unsubstituted arenesulfonyl group and any other group with or without a heteroatom(s) such as an oxygen atom(s), a nitrogen atom(s), and/or a sulfur atom(s), which does not limit reactions of this invention.

Among the substitutents, $R^1$, $R^2$, $R^3$, $R^4$, and $R^5$, as described above, a hydrogen atom, a halogen atom, a substituted or unsubstituted alkyl group, a substituted or unsubstituted aryl group, a nitro group, a cyano group, a substituted or unsubstituted alkanesulfonyl group, a substituted or unsubstituted arenesulfonyl group, a substituted or unsubstituted alkoxy group, a substituted or unsubstituted aryloxy group, a substituted or unsubstituted acyloxy group, and a substituted or unsubstituted alkoxycarbonyl group are preferable. A hydrogen atom, a halogen atom, a substituted or unsubstituted alkyl group, a substituted or unsubstituted aryl group, and a nitro group are more preferable because of their relative availability based on the starting materials.

Note that according to the nomenclature of Chemical Abstract Index Name, and in accordance with the present disclosure, for example, $C_6H_5$—$SF_5$ is named sulfur, pentafluorophenyl-; p-Cl—$C_6H_4$—$SF_5$ is named sulfur, (4-chlorophenyl)pentafluoro-; and p-$CH_3$—$C_6H_4$—$SF_5$ is named sulfur, pentafluoro(4-methylphenyl)-. $C_6H_5$—$SF_4Cl$ is named sulfur, chlorotetrafluorophenyl-; p-$CH_3$—$C_6H_4$—$SF_4Cl$ is named sulfur, chlorotetrafluoro(4-methylphenyl)-; and p-$NO_2$—$C_6H_4$—$SF_4Cl$ is named sulfur, chlorotetrafluoro(4-nitrophenyl)-.

Arylsulfur halotetrafluorides of formula (II) include isomers such as trans-isomers and cis-isomers as shown below; arylsulfur halotetrafluoride is represented by $ArSF_4X$:

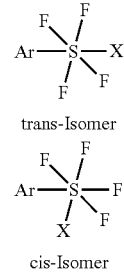

trans-Isomer cis-Isomer

Process I (Scheme 1)

Embodiments of Process I include reacting arylsulfur halotetrafluoride, having a formula (II), with hydrogen fluoride to form an arylsulfur pentafluoride having a formula (I), in which a molar ratio of arylsulfur halotetrafluoride/hydrogen fluoride is in the range of about 1/10 to about 1/150, preferably about 1/15 to about 1/100, and more preferably about 1/15 to about 1/50. When the amount of hydrogen fluoride is less than 10 mol against 1 mol of an arylsulfur halotetrafluoride, the product's yield is relatively low. When the amount of hydrogen fluoride is more than 150 mol against 1 mol of an arylsulfur halotetrafluoride, it leads to low effectiveness in production cost.

In some embodiments of the present invention the hydrogen fluoride is anhydrous or hydrous hydrogen fluoride. One particular embodiment that utilizes anhydrous hydrogen fluoride is shown in Process I. When hydrous hydrogen fluoride is used herein, the content of water must be minimized, as water may produce arylsulfonyl fluoride or arylsulfonyl chloride as byproducts, and hence the yields of the products are decreased and the separation from the byproducts becomes an issue.

The substituent(s), $R^1$, $R^2$, $R^3$, $R^4$, and $R^5$, of the products represented by the formula (I) may be different from the substituent(s), $R^1$, $R^2$, $R^3$, $R^4$, and $R^5$, of the starting materials represented by the formula (II). Thus, embodiments of this invention include transformation of the $R^1$, $R^2$, $R^3$, $R^4$, and $R^5$ to different $R^1$, $R^2$, $R^3$, $R^4$, and $R^5$ which may take place during the reaction of the present invention or under the reaction conditions, as long as the —$SF_4X$ moiety is transformed to a —$SF_5$ group.

Illustrative arylsulfur halotetrafluorides, as represented by formula (II), of the invention include, but are not limited to: phenylsulfur chlorotetrafluoride, each isomer (o-, m-, or p-isomer) of fluorophenylsulfur chlorotetrafluoride, each isomer of difluorophenylsulfur chlorotetrafluoride, each isomer of trifluorophenylsulfur chlorotetrafluoride, each isomer of tetrafluorophenylsulfur chlorotetrafluoride, pentafluorophenylsulfur chlorotetrafluoride, each isomer of chlorophenylsulfur chlorotetrafluoride, each isomer of dichlorophenylsulfur chlorotetrafluoride, each isomer of trichlorophenylsulfur chlorotetrafluoride, each isomer of bromophenylsulfur chlorotetrafluoride, each isomer of dibromophenylsulfur chlorotetrafluoride, each isomer of iodophenylsulfur chlorotetrafluoride, each isomer of chlorofluorophenylsulfur chlorotetrafluoride, each isomer of bromofluorophenylsulfur chlorotetrafluoride, each isomer of bromochlorophenylsulfur chlorotetrafluoride, each isomer of fluoroiodophenylsulfur chlorotetrafluoride, each isomer of methylphenylsulfur chlorotetrafluoride, each isomer of chloro(methyl)phenylsulfur chlorotetrafluoride, each isomer of dimethylphenylsulfur chlorotetrafluoride, each isomer of bromo(methyl)phenylsulfur chlorotetrafluoride, each isomer of bromo(dimethyl)phenylsulfur chlorotetrafluoride, each isomer of (trifluoromethyl)phenylsulfur chlorotetrafluoride, each isomer of bis(trifluoromethyl)phenylsulfur chlorotetrafluoride, each isomer of biphenylsulfur chlorotetrafluoride, each isomer of (methanesulfonyl)phenylsulfur chlorotetrafluoride, each isomer of (benzenesulfonyl)phenylsulfur chorotetrafluoride, each isomer of (trifluoromethoxy)phenylsulfur chlorotetrafluoride, each isomer of (trifluoroethoxy)phenylsulfur chlorotetrafluoride, each isomer of (tetrafluoroethoxy)phenylsulfur chlorotetrafluoride, each isomer of phenoxyphenylsulfur chlorotetrafluoride, each isomer of bromophenoxyphenylsulfur chlorotetrafluoride, each isomer of nitrophenoxyphenylsulfur chlorotetrafluoride, each isomer of nitrophenylsulfur chlorotetrafluorides, each isomer of chloro(nitro)phenylsulfur chlorotetrafluoride, each isomer of cyanophenylsulfur chlorotetrafluoride, each isomer of acetoxyphenylsulfur chlorotetrafluoride, each isomer of (benzoyloxy)phenylsulfur chlorotetrafluoride, each isomer of (methanesulfonyloxy)phenylsulfur chlorotetrafluoride, (trifluoromethanesulfonyloxy)phenylsulfur chlorotetrafluoride, each isomer of (benzenesulfonyloxy)phenylsulfur chlorotetrafluoride, each isomer of (toluenesulfonyloxy) phenylsulfur chlorotetrafluoride, each isomer of (methoxycarbonyl)phenylsulfur chlorotetrafluoride, each isomer of (ethoxycarbonyl)phenylsulfur chlorotetrafluoride, each isomer of (phenoxycarbonyl)phenylsulfur chlorotetrafluoride, each isomer of (N,N-dimethylcarbamoyl)phenylsulfur chlorotetrafluoride, each isomer of (N,N-diphenylcarbamoyl)phenylsulfur chlorotetrafluoride, each isomer of (acetylamino)phenylsulfur chlorotetrafluoride, each isomer of (N-acetyl-N-benzylamino)phenylsulfur chlorotetrafluoride, each isomer of (pentafluorosulfanyl)phenylsulfur chlorotetrafluoride, and other like compounds. Each of the above formula (II) compounds can be prepared according to reported methods (for example, see WO 2008/118787 A1, incorporated herein by reference for all purposes).

Arylsulfur halotetrafluorides (Formula II) used for the present inventions can be obtained by the reported reactions described above. For example, arylsulfur chlorotetrafluorides ($ArSF_4X$; X=Cl) are typically prepared by reaction of a diaryl disulfide (ArSSAr) or arylthiol (ArSH) with chlorine ($Cl_2$) and metal fluoride such as potassium fluoride in acetonitrile solvent as shown below (Eq 1) (see WO 2008/118787 A1).

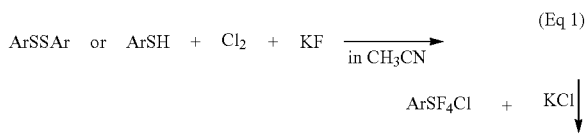

(Eq 1)

After the reaction, the reaction mixture is filtered to remove solid metal halide such as KCl and excess of solid KF, and the filtrate is concentrated under reduced pressure to give a crude product, which generally includes about 5-80 weight % of acetonitrile. In order to purify, the crude product is distilled, preferably under reduced pressure, or the crude product is recrystallized from a suitable solvent if the product is crystalline.

The distilled or crystallized products of arylsulfur halotetrafluorides (Formula II) are used for the reactions of the present inventions. The crude products arylsulfur halotetrafluorides (Formula II) mentioned above are also usable for the reactions of the present inventions [see Example 6 ($ArSF_4Cl:CH_3CN=71:29$ weight ratio), Example 8 ($ArSF_4Cl:CH_3CN=57:43$ weight ratio), and Example 14 ($ArSF_4Cl:CH_3CN=74:26$ weight ratio)]. Thus, the crude products usable for the present inventions may be the materials obtained by the filtration process to remove the metal halide and an excess of metal fluoride followed by the concentration process to remove the solvent before the final purification process such as distillation or crystallization. Using the crude product leads to significant cost reduction since the purification process, such as a distillation or crystallization, is eliminated.

From the viewpoint of cost and yield, embodiments of Process I are preferably carried out without any other solvents. However, in the case of no or low solubility of the arylsulfur halotetrafluoride and/or its product, arylsulfur pentafluoride, in hydrogen fluoride, a solvent which dissolves the arylsulfur halotetrafluoride and/or its product may be added to increase the reaction rate and yield. The preferable solvents will not substantially react with the starting materials, the final products, and/or the hydrogen fluoride. Suitable solvents include, but are not limited to, nitriles, ethers, nitro compounds, halocarbons, aromatics, hydrocarbons, and so on, and mixtures thereof. Illustrative nitriles are acetonitrile, propionitrile, benzonitrile, and other like. Illustrative ethers are diethyl ether, dipropyl ether, dibutyl ether, dioxane, glyme, diglyme, triglyme, and other like. Illustrative nitro compounds are nitromethane, nitroethane, nitrobenzene, and so on. Illustrative halocarbons are dichloromethane, chloroform, carbon tetrachloride, dichloroethane, trichloroethane, tetrachloroethane, trichlorotrifluoroethane, and other like. Illustrative aromatics are benzene, chlorobenzene, toluene, benzotrifluoride, and other like. Illustrative hydrocarbons are linear, branched, or cyclic pentane, hexane, heptane, octane, nonane, decane, and other like. Among these solvents, acetonitrile is preferable because of the high yield of the products. The amount of the solvent used can be chosen so as to promote the reaction or at least not interfere with the reaction of the arylsulfur halotetrafluoride and hydrogen fluoride.

In order to obtain a good yield of product in Process I, the reaction temperature can be selected in the range of about −80° C. to about +250° C., and preferably about −60° C. to about +200° C. A suitable temperature can be varied depending on the electron density of the benzene ring of arylsulfur halotetrafluoride, which is caused by the substituents ($R^1 \sim R^5$) on arylsulfur halotetrafluoride. The electron density is changed by the electron-donating or -withdrawing effect of the substituents ($R^1 \sim R^5$). For example, an electron-donating group increases the electron density, while an electron-withdrawing group decreases the density. The reaction proceeds at relatively low temperature with the arylsulfur halotetrafluorides having high electron density on the benzene ring, while the reactions are smooth at relatively high temperature with arylsulfur halotetrafluorides having low electron density on the benzene ring. Therefore, the reaction temperature may be chosen in order that the desired reaction be completed preferably within a week and more preferably within a few days.

Embodiments of the invention also include a method which comprises reacting an arylsulfur halotetrafluoride having a formula (II), with hydrogen fluoride in the presence of a fluoride salt having a formula, $M^+F^-(HF)_n$, to form the arylsulfur pentafluoride having a formula (I) (see Scheme 2, Process II).

Process II (Scheme 2)

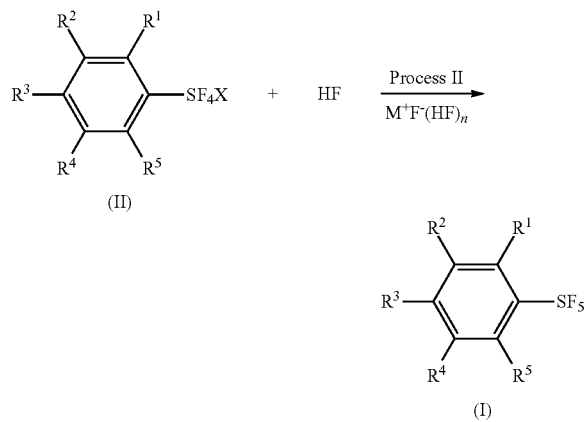

For compounds of formulas (I) and (II), $R^1$, $R^2$, $R^3$, $R^4$, $R^5$, and X are the same as defined above.

In addition, arylsulfur halotetrafluorides (Formula II) for Process II are also the same as described above in Process I.

Regarding $M^+F^-(HF)_n$, M is a cationic moiety and n is 0 or a mixed number greater than 0. Preferable M is a metal atom, an ammonium moiety, or a phosphonium moiety. Preferable fluoride salts are exemplified, but are not limited to: alkali metal fluoride salts such as LiF, NaF, KF, RbF, CsF, and their hydrogen fluoride salts such as LiF(HF)$_{n'}$, NaF(HF)$_{n'}$, KF(HF)$_{n'}$, RbF(HF)$_{n'}$, CsF(HF)$_{n'}$ in which n' is a mixed number greater than 0; alkali earth metal fluoride salts such as BeF$_2$, BeFCl, MgF$_2$, MgFCl, CaF$_2$, SrF$_2$, BaF$_2$; ammonium fluoride salts such as ammonium fluoride, methylammonium fluoride, dimethylammonium fluoride, trimethylammonium fluoride, tetramethylammonium fluoride, ethylammonium fluoride, diethylammonium fluoride, triethylammonium fluoride, tetraethylammonium fluoride, tripropylammonium fluoride, tributylammonium fluoride, tetrabutylammonium fluoride, benzyldimethylammonium fluoride, pyridinium fluoride, methylpyridinium fluoride, dimethylpyridinium fluoride, trimethylpyridinium fluoride, and other like materials, and their hydrogen fluoride salts such as NH$_4$F(HF)$_{n'}$, CH$_3$NH$_3$F(HF)$_{n'}$, (CH$_3$)$_2$NH$_2$F(HF)$_{n'}$, (CH$_3$)$_3$NHF(HF)$_{n'}$, (CH$_3$)$_4$NF(HF)$_{n'}$, (C$_2$H$_5$)$_3$NHF(HF)$_{n'}$, (C$_2$H$_5$)$_4$NF(HF)$_{n'}$, (C$_3$H$_7$)$_4$NF(HF)$_{n'}$, (C$_4$H$_9$)$_4$NF(HF)$_{n'}$, pyridine.HF(HF)$_{n'}$, and other like materials, in which n' is a mixed number greater than 0; phosphonium fluoride salts such as tetramethylphosphonium fluoride, tetraethylphosphonium fluoride, tetrapropylphosphonium fluoride, tetrabutylphosphonium fluoride, tetraphenylphosphonium fluoride, and other like materials, and their (HF)$_{n'}$ salts (n' is a mixed number greater than 0). Mixed number herein refers to whole numbers and any fraction of a whole number, e.g., 0.1, 0.2, 0.25, 0.3, 0.4, 0.5, 0.75, 0.8, 0.9, 1, 1.1, 1.2, 1.25, 1.3, 1.5, 1.75, 2, 2.5, 3, 3.5, 4, 4.5, 5, and so on.

Among the examples of fluoride salts mentioned above, alkali metal fluoride salts and their hydrogen fluoride salts are preferable, and among them, sodium fluoride and potassium fluoride and their (HF)$_{n'}$ salts are more preferable due to cost performance.

As $M^+F^-$ can react with hydrogen fluoride, $M^+F^-$ actually exists as $M^+F^-(HF)_{n'}$ (n' is a mixed number greater than 0) in hydrogen fluoride.

As a hydrogen halide, such as hydrogen chloride, is much more acidic than hydrogen fluoride, hydrogen chloride can react with the fluoride salt having a formula, $M^+F^-(HF)_n$, according to the following reaction below, to form $M^+Cl^-$ which is a neutral salt.

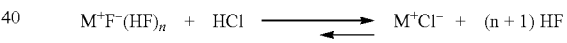

Thus, the fluoride salt can neutralize gaseous and very acidic hydrogen halide, forming a neutral salt, $M^+X^-$.

Embodiments in accordance with Process II allow for the use of either anhydrous or hydrous hydrogen fluoride. In typical cases the hydrogen fluoride is anhydrous hydrogen fluoride. However, where some amount of water is present in the process reaction, it should be minimized, as water may produce arylsulfonyl fluoride or arylsulfonyl chloride byproducts. Minimizing the water content means that it is preferable less than about 5 wt % and more preferably less than about 3 wt % of water content in the hydrogen fluoride.

The amount of hydrogen fluoride used in Process II is typically selected from the range of about 1/10 to about 1/150 of a molar ratio of arylsulfur halotetrafluoride/hydrogen fluoride. A more preferable range is about 1/15 to about 1/100, and furthermore one is about 1/15 to about 1/50. When the amount of hydrogen fluoride is less than 10 mol against 1 mol of an arylsulfur halotetrafluoride, the product's yield is relatively low. When the amount of hydrogen fluoride is more than 150 mol against 1 mol of an arylsulfur halotetrafluoride, it leads to low effectiveness in production cost.

The amount of a fluoride salt, $M^+F^-(HF)_n$, as an additive used for reactions herein is typically selected in the range of about 0.1 to about 5 mol, more preferably about 0.2 to about 3 mol, and furthermore preferably about 0.5 to about 2 mol against 1 mol of an arylsulfur halotetrafluoride. When the fluoride salt is less than 0.1 mol, the effect of the additive is too small. When it is more than 5 mol, the effect is limited.

From the viewpoint of cost and yields of the reactions, Process II is typically carried out without any other solvents. However, where there is little or no solubility of the arylsulfur halotetrafluoride and/or its product, arylsulfur pentafluoride, in hydrogen fluoride, a solvent, which dissolves the arylsulfur halotetrafluoride and/or its product, may be added to increase the reaction rate and yield. Suitable solvents for Process II are the same as for Process I mentioned above.

The reaction temperature and time are the same as for Process I as mentioned above.

Embodiments of the invention also include a method which comprises reacting an arylsulfur halotetrafluoride having a formula (II), with hydrogen fluoride in the presence of a non-fluoride salt having a formula, $M^+Y^-$ [$Y^-$ excludes $F^-(HF)_n$], to form the arylsulfur pentafluoride having a formula (I) (see Scheme 3, Process III).

Process III (Scheme 3)

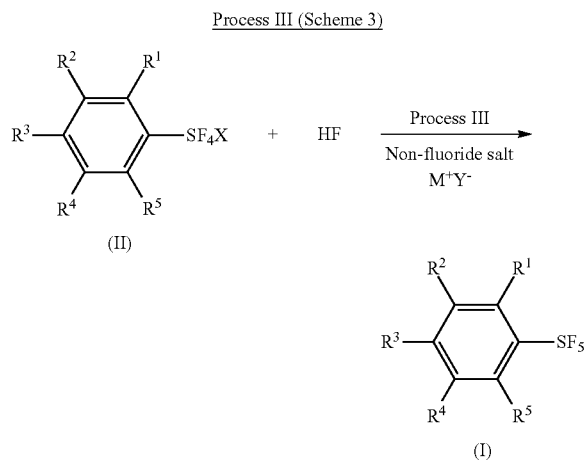

Hydrogen fluoride and its amount used in Process III is the same as for Process II, as mentioned above.

For compounds represented by formulas (I) and (II), $R^1$, $R^2$, $R^3$, $R^4$, $R^5$, and X represent the same meaning as defined previously.

Arylsulfur halotetrafluorides (Formula II) for use in Process III is the same as described in Process I.

Regarding $M^+Y^-$, M represents the same meaning as defined above, and Y is an anionic moiety [except for $F^-(HF)_n$] whose conjugated acid HY is less than HX in acidity (for example, HCl).

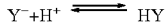

$Y^-$; a conjugated base
HY; a conjugated acid

Typical M are the same as those described for Process II. Typical Y are exemplified, but not limited to, sulfates such as $OSO_3Na$, $OSO_3K$, $OSO_3Li$, $OSO_3NH_4$, $OSO_3Mg_{1/2}$, $OSO_3Ca_{1/2}$, and other like materials; benzenesulfonate ($C_6H_5SO_3$), methylbenzenesulfonate, dimethylbenzenesulfonate, trimethylbenzenesulfonate, bromobenzenesulfonate, chlorobenzenesulfonate, nitrobenzenesulfonate, vinylbenzenesulfonate, methanesulfonate, ethanesulfonate, and other like compounds; carbonates such as $OCO_2H$, $OCO_2Na$, $OCO_2K$, $OCO_2Li$, $OCO_2NH_4$ and other like materials; carboxylates such as formate (HCOO), acetate ($CH_3COO$), propionate ($C_2H_5COO$), butanoate ($C_3H_7COO$), benzoate ($C_6H_5COO$), methylbenzoate ($CH_3C_6H_4COO$), dimethylbenzoate, trimethylbenzoate, (methoxy)benzoate, nitrobenzoate, bromobenzoate, chlorobenzoate, cinnamate ($C_6H_5CH=CHCOO$), acrylate ($CH_2=CHCOO$), 1-methylacrylate, 2-methylacrylate, 1-phenylacrylate, and other like materials.

Typical $M^+Y^-$ are exemplified, but not limited to, $NaOSO_3Na$ ($Na_2SO_4$), $KOSO_3K$ ($K_2SO_4$), $LiOSO_3Li$ ($Li_2SO_4$), $NH_4OSO_3NH_4$ [$(NH_4)_2SO_4$], $MgSO_4$, $CaSO_4$, $C_6H_5SO_3Na$, $C_6H_5SO_3K$, $C_6H_5SO_3NH_4$, $C_6H_5SO_3HNEt_3$, sodium methylbenzenesulfonate, potassium methylbenzenesulfonate, potassium dimethylbenzenesulfonate, potassium trimethylbenzenesulfonate, potassium chlorobenzenesulfonate, potassium nitrobenzenesulfonate, potassium vinylbenzenesulfonate, potassium methanesulfonate, potassium ethanesulfonate, lithium carbonate, lithium bicarbonate, sodium carbonate, sodium bicarbonate, potassium carbonate, potassium bicarbonate, lithium formate, sodium formate, potassium formate, lithium acetate, sodium acetate, potassium acetate, lithium benzoate, sodium benzoate, potassium benzoate, sodium methylbenzoate, potassium methylbenzoate, potassium dimethylbenzoate, potassium trimethylbenzoate, potassium (methoxy)benzoate, potassium nitrobenzoate, potassium bromobenzoate, potassium chlorobenzoate, potassium cinnamate, potassium propenoate (acrylate), potassium 2-methylpropenoate, potassium 2-butenoate, and other like materials.

When halogenated arylsulfur pentafluorides are formed as byproducts in the reactions of arylsulfur halotetrafluoride and hydrogen fluoride, $M^+Y^-$ is typically used, in which the anionic moiety having at least one unsaturated bond in a moiety is selected among Y mentioned above, such as benzenesulfonate ($C_6H_5SO_3$), methylbenzenesulfonate, dimethylbenzenesulfonate, trimethylbenzenesulfonate, bromobenzenesulfonate, chlorobenzenesulfonate, nitrobenzenesulfonate, vinylbenzenesulfonate, benzoate ($C_6H_5COO$), methylbenzoate ($CH_3C_6H_4COO$), dimethylbenzoate, trimethylbenzoate, (methoxy)benzoate, bromobenzenoate, chlorobenzoate, nitrobenzoate, cinnamate ($C_6H_5CH=CHCOO$), propenoate ($CH_2=CHCOO$), 2-methylpropenoate, 2-butenoate, and other like materials. The Y having at least one unsaturated bond may significantly decrease the formation of the byproducts, halogenated arylsulfur pentafluorides [see impurity (1a) of Example 26 in Table 6].

The amount of a non-fluoride salt, $M^+Y^-$, used for the reaction is typically selected in the range of about 0.1 to about 5 mol, more typically about 0.2 to about 3 mol, and furthermore typically about 0.5 to about 2 mol against 1 mol of an arylsulfur halotetrafluoride. When the non-fluoride salt is less than 0.1 mol, the effect of the fluoride salt is too low, and when it is more than 5 mol, the effect is limited.

As a hydrogen halide, such as hydrogen chloride (HCl), is more acidic than HY, hydrogen chloride can react with the non-fluoride salt having a formula, $M^+Y^-$, according to the following reaction below, to form $M^+Cl^-$, which is a neutral salt.

Thus, the non-fluoride salt can neutralize gaseous and very acidic hydrogen halide, forming a neutral salt such as $M^+X^-$.

From the viewpoint of cost and yields, Process III embodiments are typically carried out without any additional solvents. However, where there is little or no solubility of arylsulfur halotetrafluoride and/or its product, arylsulfur pentafluoride, in hydrogen fluoride, a solvent which dissolves the arylsulfur halotetrafluoride and/or its product may be added to increase the reaction rate and yield. Where appropriate, suitable solvents for Process III are the same as for Process I as mentioned above.

The reaction temperature and time for Process III are the same as for Process I, as mentioned above.

Embodiments of the invention also include a method which comprises reacting an arylsulfur halotetrafluoride having a formula (II), with hydrogen fluoride in the presence of an organic compound having one or more unsaturated bonds in a molecule to form the arylsulfur pentafluoride having a formula (I) (see Scheme 4, Process IV).

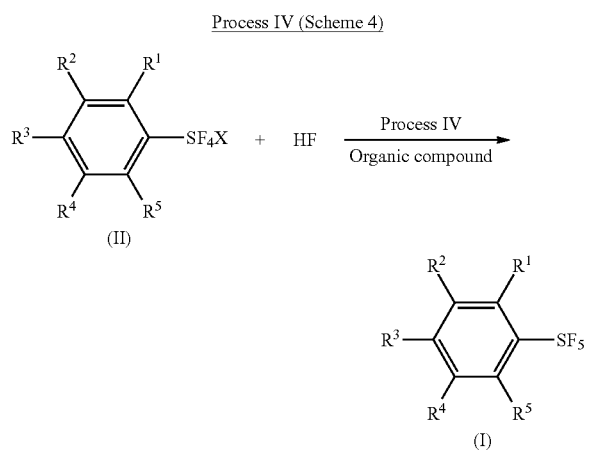

Process IV (Scheme 4)

Hydrogen fluoride and its amount used for Process IV is the same as for Process II as mentioned above.

For compounds represented by formulas (I) and (II), $R^1$, $R^2$, $R^3$, $R^4$, $R^5$, and X represent the same meaning as defined above.

Arylsulfur halotetrafluorides (Formula II) usable for Process IV are the same as described in Process I.

With regard to an organic compounds having one or more unsaturated bonds in a molecule, the organic compound is typically selected from a group consisting of arenes, alkenes, and alkynes. These organic compounds are exemplified, but not limited to, arenes such as benzene, toluene, xylene, durene, fluorobenzene, chlorobenzene, bromobenzene, phenol, anisole, cresole, naphthalene, anthracene, and other like materials; alkenes such as ethylene, vinyl chloride, vinyl bromide, vinylidene chloride, 1,2-dichloroethylene, trichloroethylene, tetrachloroethylene, propene, butene, pentene, hexene, heptene, octene, and other like materials; alkynes such as acetylene, propyne, and other like materials. Among these compounds, arenes are typical due to availability and yield of products.

When halogenated arylsulfur pentafluorides are formed as byproducts in the reactions of arylsulfur halotetrafluoride and hydrogen fluoride, the Process IV using organic compounds having one or more unsaturated bonds in a molecule are preferable because the process significantly decreases the formation of the byproducts (halogenated arylsulfur pentafluorides) [see impurity (1a) of Examples 21~25 in Table 6].

The amount of an organic compound used for the reaction is preferably selected in the range of about 0.01 mol to a large excess, against 1 mol of an arylsulfur halotetrafluoride. This may include the case where an organic compound is used as a solvent or as one of solvents for the reaction, if the organic compounds do not effect the desired reactions and are easily removed from the reaction mixture after the reaction, for example, because of low boiling point. The amount is more preferable in the range of about 0.05 mol to about 5 mol, furthermore preferably about 0.05 mol to about 1 mol against 1 mol of an arylsulfur halotetrafluoride. When it is less than 0.01 mol, the effect of the additive is too small.

From the viewpoint of cost and yields of the reactions, Process IV is preferably carried out without any other solvents. However, in the case of little or no solubility of the arylsulfur halotetrafluoride and/or its product, arylsulfur pentafluoride, in hydrogen fluoride, a solvent which dissolves the arylsulfur halotetrafluoride and/or its product may be added to increase the reaction rate and yield. Suitable solvents for Process IV are the same as for Process I mentioned above.

The reaction temperature and time for Process IV are the same as for Process I mentioned above.

Embodiments of the invention also include a method which comprises reacting an arylsulfur halotetrafluoride having a formula (II), with hydrogen fluoride in the presence of additives to form the arylsulfur pentafluoride, having a formula (I) [see Process V (Scheme 5)], in which at least two additives are selected from a group consisting of fluoride salts having a formula, $M^+F^-(HF)_n$, non-fluoride salts having a formula, $M^+Y^-$ [$Y^-$ excludes $F^-(HF)_n$], and organic compounds having one or more unsaturated bonds in a molecule.

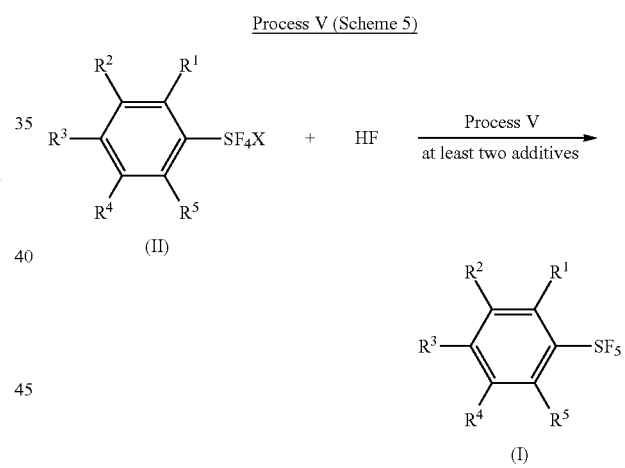

Process V (Scheme 5)

Hydrogen fluoride, and its amount used, for Process V is the same as for Process II, mentioned above.

For compounds of formulas (I) and (II), $R^1$, $R^2$, $R^3$, $R^4$, $R^5$, and X represent the same meaning as defined above.

Arylsulfur halotetrafluorides (Formula II) usable for Process V are the same as described in Process I.

The fluoride salts, $M^+F^-(HF)_n$, the non-fluoride salts, $M^+Y^-$ [$Y^-$ excludes $F^-(HF)_n$], and the organic compound having one or more unsaturated bonds in a molecule, are the same meaning as defined above.

The total amount of the additives for Process V can be selected in the range of about 0.05 mol to a large excess, more preferably about 0.1 mol to about 5 mol, and furthermore preferably about 0.5 to about 3 mol against 1 mol of an arylsulfur halotetrafluoride. The ratio between or among the additives may be chosen in order to get a better yield of the product. When the total amount of additives is less than 0.05 mol, the effect of the additive is too small.

From the viewpoint of cost and yields of the reactions, Process V is preferably carried out without any other solvents. However, in the case of little or no solubility of the arylsulfur halotetrafluoride and/or its product, arylsulfur pentafluoride, in hydrogen fluoride, a solvent which dissolves the arylsulfur halotetrafluoride and/or its product may be added to increase the reaction rate and yield. Suitable solvents for Process V are the same as for Process I mentioned above.

The reaction temperature and time for Process V are the same as for Process I mentioned above.

According to the present invention, the highly pure arylsulfur pentafluorides having the formula (I) can be cost-effectively produced in commercial production. The advancement is unexpected in light of conventional production methods both in light of costs and yield. It represents a significant hurdle to overcome the industrial aspects of the present invention as other conventional methods require high cost performance due to no fluidity of solid fluoride sources, hard control on the exothermic solid-liquid phase reactions at elevated temperature, fine purification processes necessary for products of less purity, and unsatisfactory safety and environment sustainability.

The following examples will illustrate the present invention in more detail, but it should be understood that the present invention is not deemed to be limited thereto.

EXAMPLES

Example 1

Synthesis of Phenylsulfur Pentafluoride by Reaction of Phenylsulfur Chlorotetrafluoride with Anhydrous Hydrogen Fluoride

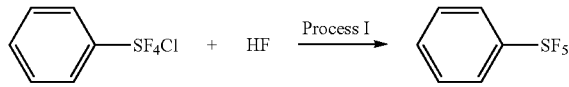

While $N_2$ gas was flowed through a 250 mL fluoropolymer (FEP) vessel set with a condenser (made of fluoropolymer), the vessel was cooled in a bath of −11° C. A coolant (−25° C.) was flowed through the condenser. The vessel cooled at −11° C. was charged with 72.3 g (3.62 mol) of anhydrous hydrogen fluoride which was cooled at −20° C. Into the vessel, 35.0 g (0.152 mol) of phenylsulfur chlorotetrafluoride (this purity was 96 wt % and the other 4 wt % was phenylsulfur trifluoride) was added over 90 min through a syringe using a syringe pump. The molar ratio of phenylsulfur chlorotetrafluoride and hydrogen fluoride was 1/24. After the addtion, the reaction mixture was stirred at −10° C. for 20 hours. After that, the reaction mixture was warmed to 25° C. and hydrogen fluoride was removed at the temperature under atmospheric pressure. The residue was mixed with 100 mL of 10% aqueous KOH and extracted with dichloromethane. The organic layer was separated, dried over anhydrous magnesium sulfate, and filtered. The filtrate was concentrated by distilling the solvent at 70° C. under atmospheric pressure. The resulting residue was distilled under reduced pressure (bath temperature about 110° C. and 32 mmHg) to give 20.6 g (yield 66%) of phenylsulfur pentafluoride. The purity of the product was determined to be 99.7% by GC analysis. The product was identified by spectral comparison with an authentic sample.

Examples 2~11

Synthesis of Arylsulfur Pentafluorides (I) by Reaction of Arylsulfur Halotetrafluorides (II) with Anhydrous Hydrogen Fluoride

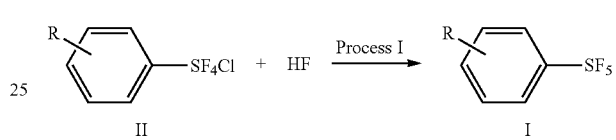

Various arylsulfur pentafluorides (I) were synthesized by reaction of the corresponding arylsulfur halotetrafluorides (II) with anhydrous hydrogen fluoride. Table 1 shows the results, the starting materials and anhydrous hydrogen fluoride used for the reactions, and reaction conditions, together with those of Example 1. The procedure was conducted in a similar way as in Example 1, except for Example 7, in which 15.0 g (46.1 mmol) of compound (II) was placed in the vessel and then mixted with liquid anhydrous hydrogen fluoride cooled at −20° C., because the compound (II) was solid. In Example 11, a mixture of 33.6 g (93.1 mmol) of compound (II) and 3.0 g of dry acetonitrile was added into the reaction vessel through a syringe. The products were identified by spectral comparison with authentic samples except for Example 11, in which, product, 4-bromo-3-fluorophenylsulfur pentafluoride, was identified by spectral analysis. Physical and spectral data of 4-bromo-3-fluorophenylsulfur pentafluoride are as follows; bp 74–79° C./6 mmHg; $^1$H NMR (CDCl$_3$) δ 7.45 (dd, J=9.0 Hz, 1.7 Hz, 1H), 7.54 (dd, J=8.6 Hz, 2.4 Hz, 1H), 7.67 (t, J=7.9 Hz, 1H); $^{19}$F NMR (CDCl$_3$) δ 63.03 (d, J=154 Hz, 4F), 82.07 (quintet, J=154 Hz, 1F), −102.98 (s, 1F); $^{13}$C NMR (CD$_3$CN) δ 113.2 (d, J=21 Hz), 114.9 (doublet-quintet, J=27 Hz, 5 Hz), 123.1 (m), 134.0 (s), 152.9 (doublet-quintet, J=7 Hz, 20 Hz), 158.2 (d, J=250 Hz); GC-Mass 302 (M$^+$), 300 (M$^+$).

TABLE 1

Synthesis of arylsulfur pentafluorides (I) by reaction of arylsulfur halotetrafluorides (II) with anhydrous hydrogen fluoride

| Ex. | (II) | HF | Mol ratio (II):HF | Conditions Temp | Time | (I) | Yield | Purity |
|---|---|---|---|---|---|---|---|---|
| 1 | ⟨phenyl⟩—SF$_4$Cl purity; 96% 35.0 g (152 mmol) | 72.3 g (3.62 mol) | 1:24 | −10° C. | 20 h | ⟨phenyl⟩—SF$_5$ | 20.6 g (66%) | 99.7% |

TABLE 1-continued

Synthesis of arylsulfur pentafluorides (I) by reaction of arylsulfur halotetrafluorides (II) with anhydrous hydrogen fluoride

| Ex. | (II) | HF | Mol ratio (II):HF | Conditions Temp | Time | (I) | Yield | Purity |
|---|---|---|---|---|---|---|---|---|
| 2 | C₆H₅—SF₄Cl<br>purity; 96%<br>20.0 g (87.1 mmol) | 82.6 g (4.13 mol) | 1:47 | 8° C. | 17 h | C₆H₅—SF₅ | 10.9 g (61%) | 99.9% |
| 3 | C₆H₅—SF₄Cl<br>purity; 96%<br>20.0 g (87.1 mmol) | 50.2 g (2.51 mol) | 1:29 | 15° C. | 20 h | C₆H₅—SF₅ | 11.0 g (62%) | 99.9% |
| 4 | 4-Cl-C₆H₄—SF₄Cl<br>purity; 91%<br>40.8 g (146 mmol) | 64.5 g (3.23 mol) | 1:22 | 15° C. | 20 h | 4-Cl-C₆H₄—SF₅ | 24.6 g (71%) | 99.2% |
| 5 | 4-F-C₆H₄—SF₄Cl<br>purity; 90%<br>23.9 g (90.2 mmol) | 51.3 g (2.57 mol) | 1:28 | 15° C. | 21 h | 4-F-C₆H₄—SF₅ | 13.5 g (67%) | 99.8% |
| 6 | 2-F-C₆H₄—SF₄Cl<br>71 wt % in CH₃CN<br>98.1 g (292 mmol) | 135 g (6.75 mol) | 1:23 | 19° C. | 22 h | 2-F-C₆H₄—SF₅ | 49.4 g (76%) | 99.0% |
| 7 | 4-Br-C₆H₄—SF₄Cl<br>purity; 92%<br>15.0 g (46.1 mmol) | 33.3 g (1.67 mol) | 1:36 | 15° C. | 22 h | 4-Br-C₆H₄—SF₅ | 9.5 g (73%) | 99.5% |
| 8 | 4-Br-C₆H₄—SF₄Cl<br>57 wt % in CH₃CN<br>131.3 g (250 mmol) | 158 g (7.90 mol) | 1:32 | 20° C. | 2 days | 4-Br-C₆H₄—SF₅ | 54.2 g (77%) | 99.9% |
| 9 | 4-H₃C-C₆H₄—SF₄Cl<br>purity; 90%<br>37.5 g (144 mmol) | 60.3 g (3.02 mol) | 1:21 | −15° C. | 20 h | 4-H₃C-C₆H₄—SF₅ | 22.2 g (71%) | 95.8% |
| 10 | 4-H₃C-C₆H₄—SF₄Cl<br>purity; 90%<br>37.5 g (144 mmol) | 63.6 g (3.18 mol) | 1:22 | 15° C. | 19 h | 4-H₃C-C₆H₄—SF₅ | 23.0 g (73%) | 90.9% |

TABLE 1-continued

Synthesis of arylsulfur pentafluorides (I) by reaction of arylsulfur halotetrafluorides (II) with anhydrous hydrogen fluoride

| Ex. | (II) | HF | Mol ratio (II):HF | Conditions Temp | Time | (I) | Yield | Purity |
|---|---|---|---|---|---|---|---|---|
| 11 | F—⌬(Br)—SF$_4$Cl purity; 88% 33.6 g (93.1 mmol) | 66.7 g (3.34 mol) | 1:36 | 5° C. → 19° C. 19° C. | 1.5 h 20.5 h | F—⌬(Br)—SF$_5$ | 18.2 g (65%) | 97.8% |

Example 12

Synthesis of Phenylsulfur Pentafluoride by Reaction of Phenylsulfur Chlorotetrafluoride with Anhydrous Hydrogen Fluoride in the Presence of K$^+$F$^-$.HF Added as an Additive

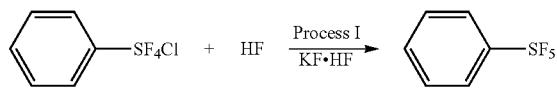

A dried 125 mL fluoropolymer (FEP) vessel was flowed with N$_2$ gas and charged with 48.0 g (2.40 mmol) of liquid anhydrous hydrogen fluoride which was cooled at −20° C. The vessel was set with a condenser (made of fluoropolymer) and a thermometer, and cooled in a bath of −20° C. A coolant (−15° C.) was flowed through the condenser. Into the vessel, 8.6 g (0.11 mol) of KF.HF was added. While the mixture was warmed to +15° C., 22.1 g (96.2 mmol) (purity 96 wt % and the other was phenylsulfur trifluoride) of phenylsulfur chlorotetrafluoride was added to the mixture over 1 hour through a syringe. The temperature of the reaction mixture was 3.4° C. and 13.6° C. at the starting point and completing point of the addition, respectively. After the addition, the reaction mixture was stirred at 15° C. for 18 h. After that, the reaction mixture was warmed to 25° C. and hydrogen fluoride was removed under atmospheric pressure. The residue was neutralized with about 15% aqueous KOH and extracted with dichloromethane. The organic layer was separated, dried over anhydrous magnesium sulfate, and filtered. The filtrate was concentrated by distilling the solvent at 70° C. under atmospheric pressure.

The resulting residue was distilled under reduced pressure to give 14.4 g (yield 73%) of phenylsulfur pentafluoride (boiling point 57.5° C./35 mmHg). The purity of the product was determined to be 100% by GC analysis. The product was identified by spectral comparison with an authentic reference sample.

Examples 13~19

Synthesis of Arylsulfur Pentafluorides (I) by Reaction of Arylsulfur Halotetrafluorides (II) with Anhydrous Hydrogen Fluoride in the Presence of a Fluoride Salt, M$^+$F$^-$(HF)$_n$, Added as an Additive

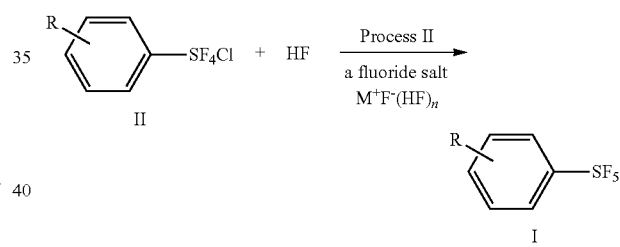

Various arylsulfur pentafluorides (I) were synthesized by reaction of the corresponding arylsulfur halotetrafluorides (II) with anhydrous hydrogen fluoride in the presence of a fluoride salt of formula, M$^+$F$^-$(HF)$_n$, added as an additive. The procedure was conducted in a similar way as in Example 12. Table 2 shows the results, the starting materials, anhydrous hydrogen fluoride, and fluoride salts used for the reactions, and reaction conditions together with those of Example 12.

TABLE 2

Synthesis of arylsulfur pentafluorides (I) by reaction of arylsulfur halotetrafluorides (II) with anhydrous hydrogen fluoride in the presence of a fluoride salt added as an additive

| Ex. | (II) | HF | Mol. ratio (II):HF | Fluoride salt added | Mol. ratio (II):Fluoride salt | Conditions | (I) | Yield | Purity |
|---|---|---|---|---|---|---|---|---|---|
| 12 | ⌬—SF$_4$Cl purity; 96% 22.1 g (96.2 mmol) | 48.0 g (2.40 mol) | 1:25 | KF•HF 8.6 g (110 mmol) | 1:1.1 | 15° C., 18 h | ⌬—SF$_5$ | 14.4 g (73%) | 100% |

TABLE 2-continued

Synthesis of arylsulfur pentafluorides (I) by reaction of arylsulfur halotetrafluorides (II) with anhydrous hydrogen fluoride in the presence of a fluoride salt added as an additive

| Ex. | (II) | HF | Mol. ratio (II):HF | Fluoride salt added | Mol. ratio (II):Fluoride salt | Conditions | (I) | Yield | Purity |
|---|---|---|---|---|---|---|---|---|---|
| 13 | F—⟨C6H4⟩—SF4Cl<br>purity; 90%<br>35.8 g (135 mmol) | 59.3 g<br>(2.97 mol) | 1:22 | KF•HF<br>12.9 g<br>(165 mmol) | 1:1.2 | 15° C., 2 days | F—⟨C6H4⟩—SF5 | 20.1 g<br>(67%) | 99.8% |
| 14 | 3-F-C6H4-SF4Cl<br>74 wt % in CH3CN<br>96.6 g (300 mmol) | 217 g<br>(10.9 mol) | 1:36 | KF•HF<br>23.4 g<br>(300 mmol) | 1:1 | −20 -> 10° C., 2 h<br>10° C., 15 h<br>15° C., 6 h | 3-F-C6H4-SF5 | 40.6 g<br>(61%) | 100% |
| 15 | H3C—⟨C6H4⟩—SF4Cl<br>purity; 90%<br>23.4 g (89.8 mmol) | 40.1 g<br>(2.0 mol) | 1:22 | KF•HF<br>8.6 g<br>(110 mmol) | 1:1.2 | 15° C., 20 h | H3C—⟨C6H4⟩—SF5 | 15.4 g<br>(79%) | 97.2% |
| 16 | H3C—⟨C6H4⟩—SF4Cl<br>purity; 90%<br>33.4 g (128 mmol) | 70.6 g<br>(3.53 mol) | 1:28 | LiF<br>4.1 g<br>(152 mmol) | 1:1.2 | −15° C., 16 h | H3C—⟨C6H4⟩—SF5 | 17.4 g<br>(62%) | 96.3% |
| 17 | H3C—⟨C6H4⟩—SF4Cl<br>purity; 90%<br>37.5 g (144 mmol) | 58.8 g<br>(2.94 mol) | 1:20 | NaF•HF<br>10.9 g<br>(176 mmol) | 1:1.2 | 15° C., 18 h | H3C—⟨C6H4⟩—SF5 | 22.2 g<br>(71%) | 97.0% |
| 18 | H3C—⟨C6H4⟩—SF4Cl<br>purity; 90%<br>37.5 g (144 mmol) | 47.0 g<br>(2.35 mol) | 1:16 | KF•HF<br>21.8 g<br>(279 mmol) | 1:1.9 | 15° C., 19 h | H3C—⟨C6H4⟩—SF5 | 17.4 g<br>(55%) | 97.2% |
| 19 | 3,4-F2-C6H3-SF4Cl<br>purity; 88%<br>12.8 g (43.9 mmol) | 71.3 g<br>(3.57 mol) | 1:81 | KF•HF<br>3.9 g<br>(50 mmol) | 1:1.1 | −5 -> 15° C., 2.5 h<br>15° C., 16.5 h | 3,4-F2-C6H3-SF5 | 52 g<br>(49%) | 96.6% |

The products were identified by spectral comparison with reference samples, except for Example 19, in which, the product, 3,4-difluorophenylsulfur pentafluoride, was identified by spectral analysis. Physical and spectral data of 3,4-difluorophenylsulfur pentafluoride are as follows: bp 75-76° C./25 mmHg; $^1$H NMR (CDCl$_3$) δ 7.27 (m, 1H), 7.53-7.58 (m, 1H), 7.62-7.66 (m, 1H); $^{19}$F NMR (CDCl$_3$) δ −133.75 (d, J=26 Hz, 1F), −130.93 (d, J=26 Hz, 1F), 63.60 (d, J=147 Hz, 4F), 82.56 (quintet, J=147 Hz, 1F); $^{13}$C NMR (CDCl$_3$) δ 116.6 (dt, J=22 Hz, 4 Hz), 117.4 (d, J=19 Hz), 123.0 (m), 49.2 (quintet, J=20 Hz), 149.3 (dd, J=254 Hz, 13 Hz), 152.0 (dd, J=257 Hz, 12 Hz); GC-Mass 240 (M$^+$).

As mentioned above, the fluoride salt can neutralize hydrogen chloride which is formed from the reaction. Furthermore, for examples, as seen from the comparison between Examples 3 and 12 and between Examples 10 and 15 at the same reaction temperature, the addition of a fluoride salt can make the yield and purity of the products higher than without the additive because the additive can make the reactions mild and surpress the formation of tar.

Example 20

Synthesis of Arylsulfur Pentafluoride (I) by Reaction of Arylsulfur Halotetrafluoride (II) with Anhydrous Hydrogen Fluoride in the Presence of a Non-Fluoride Salt

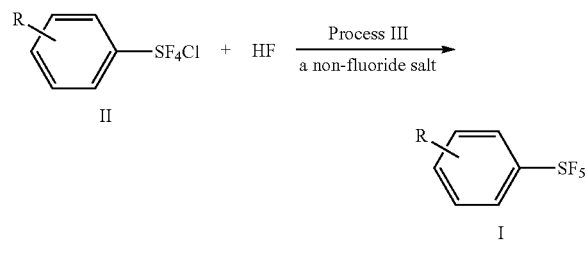

Liquid anhydrous hydrogen fluoride (61 g, 3.05 mol) was put in a dried 125 mL fluoropolymer vessel in the same way as in Example 12. The vessel was then set with a condenser (made of fluoropolymer) and a thermometer, and cooled in a bath of −20° C. Sodium acetate (9.0 g, 0.11 mol) was added portion by portion into a stirred liquid of hydrogen fluoride in the vessel. The mixture was homogenious. A coolant (−15° C.) was flowed through the condenser and the bath temperature was raised to −10° C. Phenylsulfur chlorotetrafluoride (23.4 g, purity 95 wt %, 0.101 mol) was added to the mixture over 30 min through a syringe using a syringe pump. The temperature of the reaction mixture was −8° C. and −6° C. at the starting point and completing point of the addition, respectively. The bath temperature was then raised to +5° C. and the reaction mixture was stirred for 70 min at +5° C. The bath temperature was then raised to +10° C. and the reaction mixture was stirred for 50 min. The bath temperature was then raised to +15° C. and the reaction mixture was stirred for 20 h at +15° C. After the reaction, the bath temperature was warmed to room temperature and hydrogen fluoride was removed by evaporation at room temperature. The residue was slowly poured into 400 g of 23% aqueous KOH solution, and the mixture was stirred for 30 min. The lower organic layer was separated and the upper aqueous layer was extracted with dichloromethane. The combined organic layer was washed with saturated aqueous NaCl solution, dried over anhydrous magnesium sulfate, and filtered. The filtrate was concentrated by distilling the solvent on an oil bath of 70° C. at atmospheric pressure. The resulting residue was distilled by heating in an oil bath of 180° C. and more at atmospheric pressure, giving 11.5 g of phenylsulfur pentafluoride which was a fraction of 145-150° C. The purity of the product was determined to be 99.6% by GC analysis. The product was identified by spectral comparison with a reference sample. Table 3 summarizes the reaction conditions and results.

TABLE 3

Synthesis of arylsulfur pentafluorides (I) by reaction of arylsulfur halotetrafluorides (II) with hydrogen fluoride in the presence of a non-fluoride salt

| Ex. | (II) | HF | Mol. ratio (II):HF | Non-fluoride salt | Mol. ratio (II):non-fluoride salt | Conditions | (I) | Yield | Purity |
|---|---|---|---|---|---|---|---|---|---|
| 20 | ⟨phenyl⟩—SF$_4$Cl purity; 95% 23.4 g (101 mmol) | 61 g (3.06 mol) | 1:30 | NaOCOCH$_3$ 9.0 g (110 mmol) | 1:1.1 | 5° C. -> 10° C., 2 h 15° C., 20 h | ⟨phenyl⟩—SF$_5$ | 11.5 g (56%) | 99.6% |

Example 21

Synthesis of Arylsulfur Pentafluoride (I) by Reaction of Arylsulfur Halotetrafluoride (II) with Anhydrous Hydrogen Fluoride in the Presence of an Organic Compound

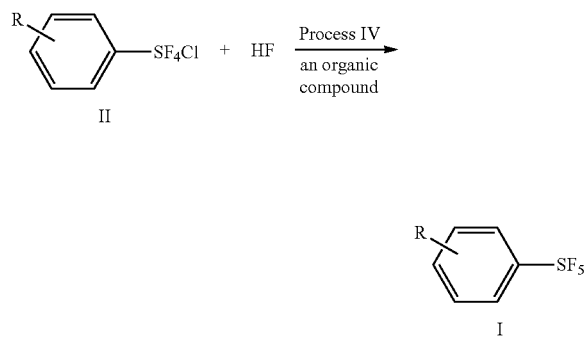

Example 21 was conducted in a similar way as in Example 12 except that an organic compound was added in place of a fluoride salt. Table 4 shows the starting material, anhydrous hydrogen fluoride, and an aromatic compound as an additive used for the reaction, reaction conditions, and results. The product was identified by comparison with a reference sample.

Examples 22~26

Synthesis of Arylsulfur Pentafluorides (I) by Reaction of Arylsulfur Halotetrafluorides (II) with Anhydrous Hydrogen Fluoride in the Presence of Two or More Additives Selected from a Group Consisting of Fluoride Salts, Non-Fluoride Salts, and Organic Compounds Various arylsulfur pentafluorides (I) were synthesized by reaction of the corresponding arylsulfur halotetrafluorides (II) with anhydrous hydrogen fluoride in the presence of two or more additives, which are selected from a group consisting of fluoride salts, non-fluoride salts, and organic compounds having one or more unsaturated bonds in a molecule. The reaction was conducted in a similar way as in Example 12 except that two or more additives were added in place of a fluoride salt. Examples 22~25 were performed with a fluoride salt and an organic compound as additives, and Example 26 was performed with a fluoride salt and a non-fluoride salt as additives. The product was identified by comparison with a reference sample.

Table 5 shows the results, the starting material, anhydrous hydrogen fluoride, and additives used for the reactions, and reaction conditions. According to this method using two or more additives, products of high purity were obtained in better relative yields. At the same reaction temperature (+15° C.), the purities of the products of Examples 22~26 (96~99%) are much higher than those of Example 10 (90.9%) without any additive and Example 21 (90%) with one additive (benzene).

TABLE 4

Synthesis of arylsulfur pentafluorides (I) by reaction of arylsulfur halotetrafluorides (II) with hydrogen fluoride in the presence of an organic compound

| Ex. | (II) | HF | Mol ratio (II):HF | Organic compound | Mol. ratio (II):organic compound | Conditions | (I) | Yield | Purity |
|---|---|---|---|---|---|---|---|---|---|
| 21 | CH$_3$—C$_6$H$_4$—SF$_4$Cl<br>purity; 81%<br>23.4 g (80.8 mmol) | 48.6 g (2.4 mol) | 1:30 | Benzene 2.7 mL (30 mmol) | 1:0.37 | 15° C. 79 h | CH$_3$—C$_6$H$_4$—SF$_5$ | 10.1 g (57%) | 90% |

A byproduct, 3-chloro-4-methylphenylsulfur pentafluoride (1a), formed in Example 21 is shown in Table 6. As a comparison (at the same reaction temperature), Example 10 without any additive is also shown in Table 6. The byproduct (1a) was 1.0% in Example 21, while byproduct (1a) was 8.1% in Example 10. This clearly indicates that an organic compound (benzene) as an additive greatly prevents the formation of byproduct (1a) by washing out the side reactions (chlorination of the product). This provides a surprising advantage over other conventional synthesis reactions.

TABLE 5

Synthesis of arylsulfur pentafluorides (I) by reaction of arylsulfur halotetrafluorides (II) with hydrogen fluoride in the presence of at least two additives selected from a group consisting of fluoride salts, non-fluoride salts, and organic compounds

| Ex. | (II) | HF | Mol. rtio (II):HF | Additives (A) | Additives (B) | Mol. ratio (II):(A):(B) | Conditions | (I) | Yield | Purity |
|---|---|---|---|---|---|---|---|---|---|---|
| 22 | $CH_3$—C$_6$H$_4$—$SF_4Cl$ purity; 90% 23.4 g (89.8 mmol) | 46.2 g (2.31 mol) | 1:26 | KF•HF 8.6 g (0.11 mol) | Benzene 0.9 mL (10 mmol) | 1:1.2:0.11 | 15° C. 15 h | $CH_3$—C$_6$H$_4$—$SF_5$ | 15.1 g (77%) | 96% |
| 23 | $CH_3$—C$_6$H$_4$—$SF_4Cl$ purity; 86% 23.4 g (85.8 mmol) | 38.6 g (1.9 mol) | 1:22 | KF•HF 8.6 g (0.11 mol) | Benzene 1.8 mL (20 mmol) | 1:1.3:0.23 | 15° C. 21 h | $CH_3$—C$_6$H$_4$—$SF_5$ | 13.1 g (70%) | 98.1% |
| 24 | $CH_3$—C$_6$H$_4$—$SF_4Cl$ purity; 94.5% 23.4 g (94.3 mmol) | 45.8 g (2.3 mol) | 1:24 | KF•HF 8.6 g (0.11 mol) | Benzene 2.2 mL (25 mmol) | 1:1.2:0.27 | 15° C. 19 h | $CH_3$—C$_6$H$_4$—$SF_5$ | 13.3 g (65%) | 98% |
| 25 | $CH_3$—C$_6$H$_4$—$SF_4Cl$ purity; 92% 23.4 g (91.8 mmol) | 43.1 g (2.15 mol) | 1:23 | KF•HF 8.6 g (0.11 mol) | Benzene 2.7 mL (30 mmol) | 1:1.2:0.33 | 15° C. 17 h | $CH_3$—C$_6$H$_4$—$SF_5$ | 11.3 g (56%) | 99% |
| 26 | $CH_3$—C$_6$H$_4$—$SF_4Cl$ purity; 79% 23.4 g (78.8 mmol) | 56.9 g (2.85 mol) | 1:36 | KF•HF 6.4 g (82 mmol) | $CH_3$—C$_6$H$_4$—$SO_3K$ 6.0 g (29 mmol) | 1:1.0:0.37 | 15° C. 17 h | $CH_3$—C$_6$H$_4$—$SF_5$ | 12.6 g (73%) | 97.5% |

For a more detailed discussion, Table 6 shows the contents of impurity (Ia) and other byproducts (IIIa~c) contained in the products obtained in Examples 10, 15, and 21~26. The formation of impurity (1a) decisively hurts the yields and purity of products (I). Other byproducts (IIIa~c) do not hurt the reaction because they depend on the additives and hence suitable reaction conditions or suitable additives can be selected for the reaction. Example 10 was conducted without any additives, Example 15 was conducted with KF.HF as one additive, Example 21 was conducted with benzene as one additive, Examples 22~25 were conducted with KF.HF and benzene as two additives, and Example 26 was conducted with KF.HF and potassium p-methylbenzenesulfonate as two additives. The amount of impurity (1a) was 8.1% in Example 10, 1.9% in Example 15, 1.0% in Example 21, and 0.2% in Examples 22, no formation in Examples 23~25, and 0.7% in Example 26. It is clear that KF.HF or benzene as one additive significantly prevents the formation of the impurity (1a), and that the use of both KF.HF and benzene or potassium p-methylbenzenesulfonate as two additives almost or completely eliminate the formation of the impurity (1a). Thus, the impurity is significantly decreased or completely not formed by these additives. Again, this shows the utility of the present invention.

TABLE 6

Contents of impurity (Ia) and other byproducts (IIIa~c) contained in the products obtained in Examples 10, 15, and 21-26

| Ex. | Mol. ratio (II):(A):(B) (A) = KFHF (B) = benzene or p-Me—PhSO₃K | Product (I) | Impurity[1] (Ia) CH₃–C₆H₃(Cl)–SF₅ | Other byproducts[1] Cl–C₆H₅ (IIIa) | Cl–C₆H₄–Cl (IIIb) | Cl–C₆H₄–Cl (ortho) (IIIc) |
|---|---|---|---|---|---|---|
| 10 | (II) alone | CH₃–C₆H₄–SF₅ | 8.1% | no | no | no |
| 15 | (II):(A) 1:1.2 | CH₃–C₆H₄–SF₅ | 1.9% | no | no | no |
| 21 | (II):(B) 1:0.37 | CH₃–C₆H₄–SF₅ | 1.0% | n.d. | 6.2% | 3.1% |
| 22 | (II):(A):(B) 1:1.2:0.11 | CH₃–C₆H₄–SF₅ | 0.2% | 0.4% | 1.8% | 1.8% |
| 23 | (II):(A):(B) 1:1.3:0.23 | CH₃–C₆H₄–SF₅ | n.d. | 0.7% | 0.4% | 0.2% |
| 24 | (II):(A):(B) 1:1.2:0.27 | CH₃–C₆H₄–SF₅ | n.d. | 1.1% | 0.7% | 0.3% |
| 25 | (II):(A):(B) 1:1.2:0.33 | CH₃–C₆H₄–SF₅ | n.d. | 0.4% | 0.3% | 0.2% |
| 26 | (II):(A):(B) 1:1.0:0.37 | CH₃–C₆H₄–SF₅ | 0.7% | no | no | no |

[1] Contents were determined by GC analysis. no = no formation. n.d. = not detected.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims. All publications cited herein are hereby incorporated by reference.

What is claimed is:

1. A method for preparing arylsulfur pentafluoride having a formula (I) as follows:

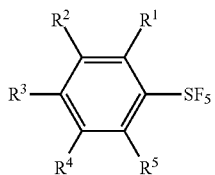

(I)

comprising reacting arylsulfur halotetrafluoride of formula (II) with anhydrous hydrogen fluoride to form the arylsulfur pentafluoride:

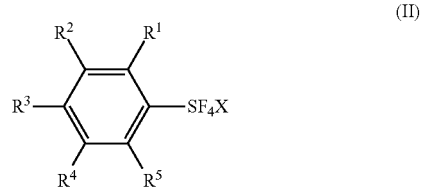

(II)

wherein a mol ratio of the arylsulfur halotetrafluoride to anhydrous hydrogen fluoride is in the range of about 1:10 to about 1:150;

in which: $R^1$, $R^2$, $R^3$, $R^4$, and $R^5$ each is independently a hydrogen atom, a halogen atom, a substituted or unsubstituted alkyl group having 1 to 18 carbon atoms, a substituted or unsubstituted aryl group having 6 to 30 carbon atoms, a nitro group, a cyano group, a substituted or unsubstituted alkanesulfonyl group having 1 to 18 carbon atoms, a substituted or unsubstituted arenesulfonyl group having 6 to 30 carbon atoms, a substituted or unsubstituted alkoxy group having 1 to 18 carbon atoms, a substituted or unsubstituted aryloxy group having 6 to 30 carbon atoms, a substituted or unsubstituted acyloxy group having from 1 to 18 carbon atoms, a substituted or unsubstituted alkanesulfonyloxy group having from 1 to 18 carbon atoms, a substituted or unsubstituted arenesulfonyloxy group having from 6 to 30 carbon atoms, a substituted or unsubstituted alkoxycarbonyl group having 2 to 18 carbon atoms, a substituted or unsubstituted aryloxycarbonyl group having 7 to 30 carbon atoms, a substituted carbamoyl group having 2 to 18 carbon atoms, a substituted amino group having 1 to 18 carbon atoms, or a $SF_5$ group; and X is a chlorine atom, bromine atom, or iodine atom.

2. The method of claim 1 wherein the mol ratio of the arylsulfur halotetrafluoride to the hydrogen fluoride is in the range of about 1:15 to about 1:100.

3. The method of claim 1 wherein X is Cl.

* * * * *